United States Patent [19]
Purdy et al.

[11] Patent Number: 5,535,771
[45] Date of Patent: Jul. 16, 1996

[54] VALVED PRN ADAPTER FOR INFUSION DEVICES

[75] Inventors: E. Robert Purdy, Fruit Heights; Mark A. Crawford, Sandy; Timothy J. Erskine; Gerald H. Peterson, both of Salt Lake City, all of Utah

[73] Assignee: Becton, Dickinson and Company, Franklin Lakes, N.J.

[21] Appl. No.: 288,171

[22] Filed: Aug. 10, 1994

[51] Int. Cl.$^6$ .................................................... F16L 37/28
[52] U.S. Cl. ..................... 137/15; 251/149.1; 604/256; 604/905
[58] Field of Search ................................. 604/256, 905; 251/149.1; 137/15, 315

[56] References Cited

U.S. PATENT DOCUMENTS

| | | | |
|---|---|---|---|
| 4,934,655 | 6/1990 | Blenkush et al. | 251/149.1 |
| 5,085,645 | 2/1992 | Purdy et al. | 604/256 |
| 5,108,380 | 4/1992 | Herlitze et al. | 604/283 |
| 5,251,873 | 10/1993 | Atkinson et al. | 251/149.1 |
| 5,269,771 | 12/1993 | Thomas et al. | 604/213 |
| 5,289,849 | 3/1994 | Paradis | 251/149.1 |

*Primary Examiner*—A. Michael Chambers
*Attorney, Agent, or Firm*—Arthur D. Dawson

[57] ABSTRACT

A valved adapter for a medical access device includes a body with a longitudinal axis. The body has a proximal first end, a distal second end and a passageway therethrough which has an inside surface. The passageway has a chamber defined by a proximal shoulder and a segmented distal shoulder both projecting inwardly from the surface of the passageway. The chamber is located intermediate the first end and second end of the body. The adapter includes a valve contained within the chamber for selectively obstructing and allowing fluid flow through the passageway. The valve includes an elongate resilient member with an axis substantially coaxial to the longitudinal axis of the body having a proximal end and a distal end. The elongate resilient member is axially compressed between the distal shoulder and the proximal shoulder, the compression biasing the valve to a normally closed position. The proximal end of the resilient member forms a substantially fluid tight seal with the proximal shoulder which obstructs fluid flow through the passageway. The adapter further includes a pusher for selectively further axially compressing the resilient member so that the proximal end of the adapter no longer forms a fluid tight seal with the proximal shoulder thereby allowing fluid flow through the passageway. The adapter includes fittings for attaching the adapter to a medical access device and for attaching fluid delivery devices to the adapter.

19 Claims, 5 Drawing Sheets

VALVED PRN ADAPTER FOR INFUSION DEVICES

FIELD OF THE INVENTION

The present invention relates to infusion devices and more particularly to a valved adapter useful with a variety of medical access devices.

BACKGROUND OF THE INVENTION

Medical access devices, particularly infusion devices, over-the-needle catheters, other catheters and feeding tubes are important tools for administration of fluids to patients. After placement, in normal management of a catheter or other medical access device in a patient, it is often necessary to be able to add or withdraw fluids through the device. In many surgical procedures, it is routine to place an intravenous catheter so that if it is necessary to medicate a patient during a procedure, the catheter already is in place. In other types of procedures it is necessary to periodically administer medicaments through the device or to withdraw samples. In all of these applications, it is desirable that the device include a valve mechanism that will open to allow the administration and to close the device after the administration.

U. S. Pat. No. 5,085,645 teaches an over-the-needle catheter having an integral valve in a passage in the catheter hub. The patent discloses a valve adapter that is an integral part of a catheter hub.

U. S. Pat. No. 5,251,873 teaches a medical coupling site that is adapted to be attached directly to a standard male luer lock fitting. The coupling site includes a valve element contained within a tubular retainer. The coupling site includes a slit rubber diaphragm valve that is deflected by introduction of a male luer fitting and closes by the removal of the male luer. According to international standards, there is an allowable range of 2.5 mm in engagement length of a luer fitting. This variation in engagement length occurs because of variation in the outside diameter of the male projection and the inside diameter of the female receptacle of the luer fittings. Thus, a "fat" male luer will result in a "short" engagement length and conversely. Valves of the type disclosed in U. S. Pat. No. 5,251,873 may not open fully with male luer fittings at the "short" end of the allowable dimension, and since they also depend on the diaphragm for sealing around the male luer tip, they may also leak, they may also leak when a male fitting is mounted or may not fully close once opened.

U. S. Pat. No. 5,108,380 discloses a valve device for a hub member of a catheter. The valve is actuated by the placement of a male luer fitting which displaces a piston biased by a coil spring to open the valve.

U. S. Pat. No. 5,269,771 discloses a needleless introducer with a hemostatic valve. The valve mechanism includes a plunger biased by a coil spring which, upon actuation, spreads a pair of resilient valve elements. This design may not be fully opened by a male luer fitting at the "short" side of the dimension, and the sealing depends upon the resilient valve elements closing against themselves. Further the valve uses several different materials and is complex to assemble.

Valves and adapters of the type described above fall into a medical device category often referred to as "PRN" from the Latin pro re nata, i.e., as the circumstances may require. A typical example of this type usage might be on a catheter left in place for three days. During this three day usage duration, a bolus dosage of a medicament might be given every 4 hours using a protocol including at each dosage interval: a) flushing the catheter to check patency; b) administration of the medicament; and c) flushing the medicament from the catheter with heparin or saline. During the period of usage, this typical protocol results in 54 operations of the valve, i.e., 6 times a day, 3 steps each time and 3 days. In between each dosage, the valve must not leak, but it must be readily reopened. Previously, the introduction may have been made using hypodermic needles penetrating a resilient septum. However, a septum is likely to start leaking after multiple penetrations and given the concerns about risks to practitioners and service personnel from "sharps," hospitals have changed many protocols to reduce the use of pointed hypodermic needles. The PRN adapters as described above have been developed to address the hospitals' needs.

While the teachings cited above address many of the practitioners' concerns, there is still a need for a valved adapter for medical access devices that offers rapid, easy-to-use access with automatic positive on/off flow control. A device having these features plus the advantage of being easily closed by a protective cap and simple to manufacture is disclosed below.

SUMMARY OF THE INVENTION

The present invention is a simple-to-manufacture valved adapter for medical access devices. The adapter may be readily attached to medical access devices such as feeding tubes, vascular access devices, and the like. The valved adapter provides rapid access for mounting and dismounting fluid handling devices to medical access devices such as catheters. The adapter of the present invention provides positive automatic starting and stopping of fluid flow through the device with mounting and dismounting of fluid handling devices onto vascular access devices. The adapter of the present invention minimizes exposure of medical practitioners to patient body fluids, eliminates the need for "sharps" to connect to medical access devices and minimizes the chance of air introduction to the patient during fluid handling device transfers. An added benefit of the present invention is that patient blood loss, in the event of an unintentional disconnect, is minimized.

A valved adapter for a medical access device includes a body with a longitudinal axis. The body has a proximal first end, a distal second end and a passageway therethrough that has an inside surface. The passageway has a chamber defined by a proximal shoulder and a segmented distal shoulder projecting inwardly from the surface of the passageway. The chamber is located intermediate the first end and second end of the body. The adapter includes a valve contained within the chamber for selectively obstructing and allowing fluid flow through the passageway. The valve includes an elongate resilient member with an axis substantially coaxial to the longitudinal axis of the body having a proximal end and a distal end. The elongate resilient member is axially compressed between the proximal shoulder and the distal shoulder, the compression biasing the valve to a normally closed position. The proximal end of the resilient member forms a substantially fluid tight seal with the proximal shoulder. The seal obstructs fluid flow through the passageway. The adapter further includes a pusher for selectively further axially compressing the resilient member so that the proximal end no longer forms a substantially fluid tight seal with the proximal shoulder thereby allowing fluid flow through the passageway.

The valved adapter preferably includes fittings at the proximal and distal ends for mounting the adapter to medical access devices and for attachment of fluid delivery devices. These fittings may include threads, luer, snap-fit, bayonet and similar devices where the fitting on the delivery device being attached preferably includes provisions for engaging the pusher when the fluid delivery device is mounted. In a preferred embodiment the valved adapter has a proximal female luer fitting and a distal male luer fitting. Preferably, the pusher extends proximally within the passageway so that when a fluid handling device having a male luer fitting is mounted on the proximal female luer fitting, the male fitting engages the pusher, opening the valve and allowing fluid flow through the passageway.

A method for assembling a valved adapter for a device of the present invention includes providing a two part body with a longitudinal axis having a proximal first end, a distal second end and a passageway having an inside surface therethrough. The passageway has a chamber defined by proximal shoulder and a segmented distal shoulder projecting inwardly from the surface of the passageway. The distal shoulder has openings therethrough between the segments. The chamber is intermediate the first end and second end of the body. The two part body includes a distal part and a proximal part with a parting line located transverse the longitudinal axis and intermediate the shoulders. The method further includes providing a valve to be contained within the chamber for selectively obstructing and allowing fluid flow through the passageway. The valve includes an elongate resilient member having an axis substantially coaxial to the longitudinal axis of the body with a distal end and a proximal end. The resilient member is axially compressed between the proximal shoulder and the distal shoulder. The compression of the elongate resilient member serves to bias the valve to a normally closed position with the proximal end of the resilient member forming a fluid tight seal with the proximal shoulder thereby obstructing fluid flow through the passageway.

The method further includes providing a pusher for selectively further axially compressing the elongate resilient member so that the proximal end of the elongate resilient member no longer forms the fluid tight seal with the proximal shoulder thus allowing fluid flow through the passageway.

The method includes placing the elongate resilient member in the distal part so that the distal end of the resilient member is in contact with the segmented distal shoulder. The method then further includes placing the pusher into the elongate resilient member so that the proximal extension of the pusher extends proximally from the resilient member. The method for assembly then includes axially placing the proximal part of the body on the distal part so that the proximal end of the elongate resilient member is within the chamber thereby axially compressing the elongate resilient member and biasing the valve to the normally closed position. The distal part and the proximal parts of the body are then fixedly attached, completing the assembly of the valved adapter.

DETAILED DESCRIPTION OF THE INVENTION

Figure 1:
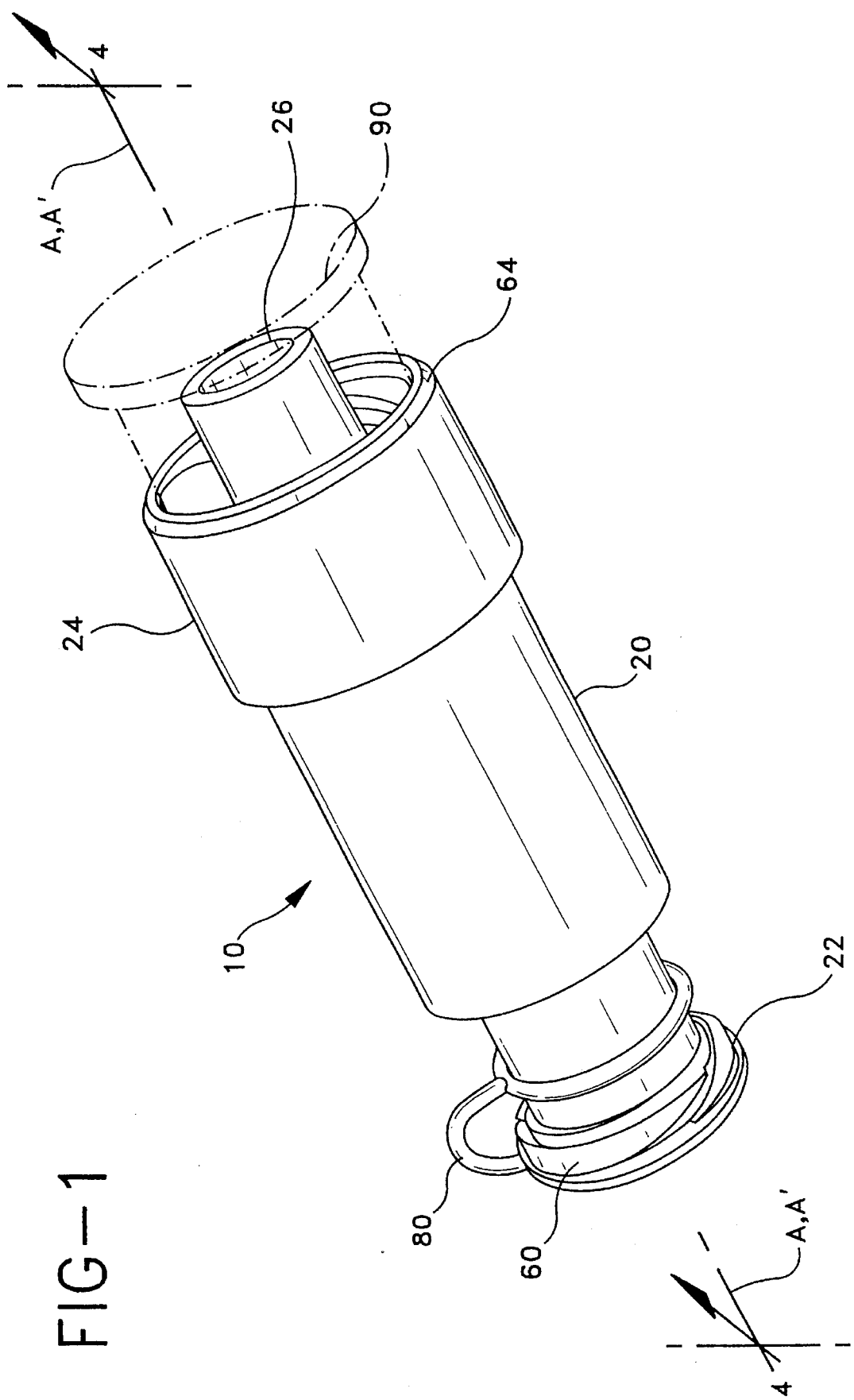
FIG. 1 is a perspective view of an adapter of the present invention.
Figure 2:
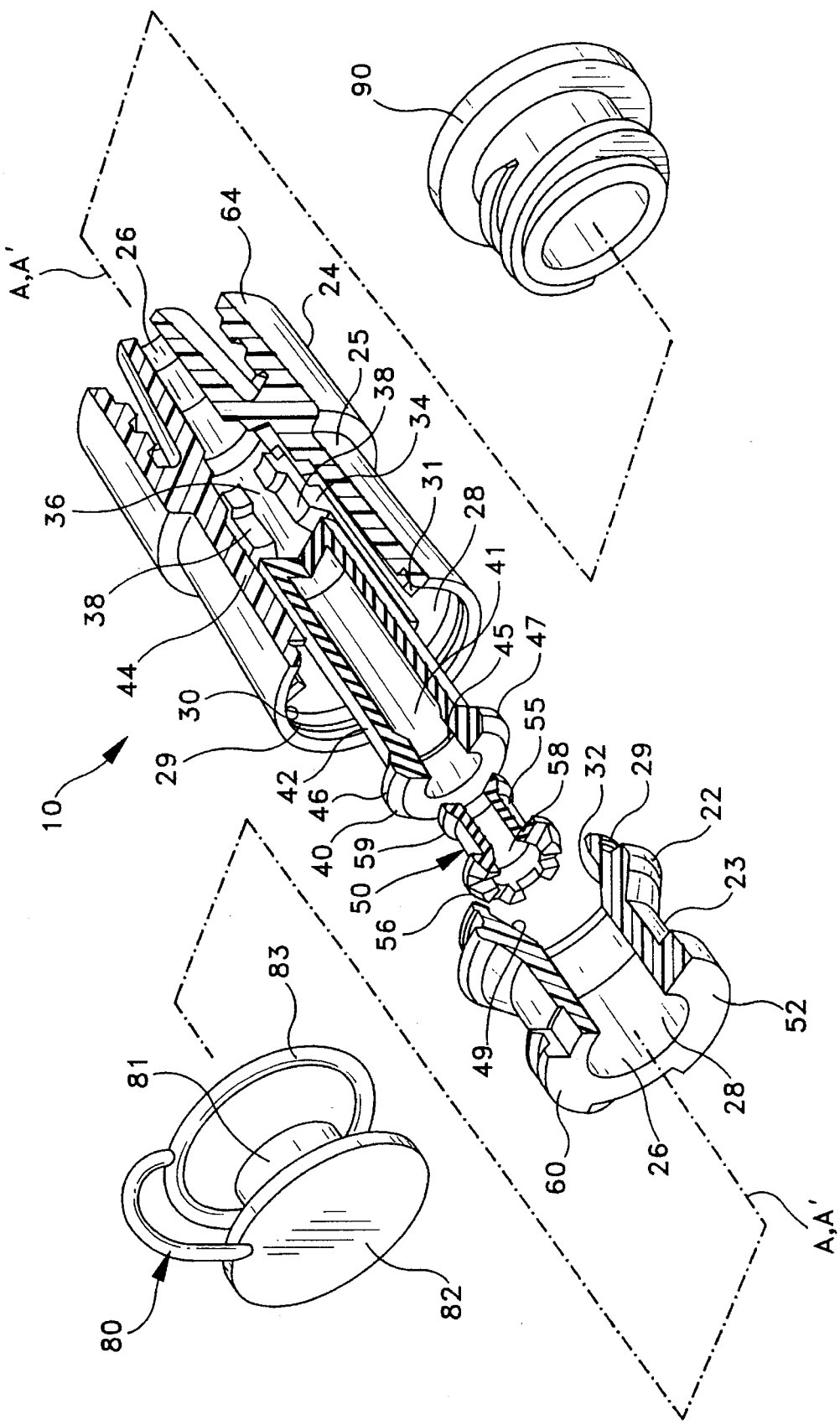
FIG. 2 is an exploded cut-away perspective view of an adapter of the present invention.
Figure 3:
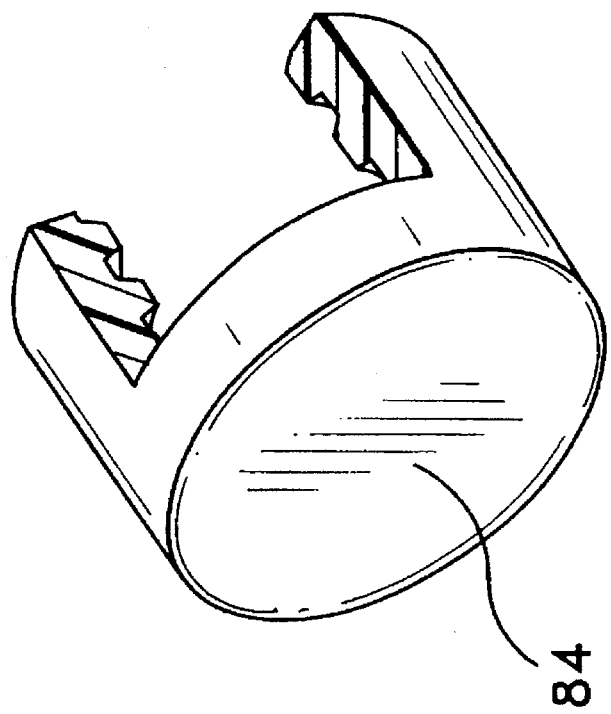
FIG. 3 is a cut-away perspective view of a cap for the adapter of the present invention.

While this invention is satisfied by embodiments in many different forms, there is shown in the drawings and will herein be described several embodiments of the invention with the understanding that the present disclosure is to be considered descriptive of the principles of the present invention and is not intended to limit the scope of the invention to the embodiments illustrated. The scope of the invention will be measured by the appended claims and their equivalents.

Referring to FIGS. 1–4, a valved adapter 10 of the present invention for a medical access device includes a substantially cylindrical body 20 with a longitudinal axis A, a proximal first end 22 and a distal second end 24. Body 20 has a passageway. 26 with an inside surface 28. Passageway 26 includes a chamber 30 having a plurality of axial channels 31. Chamber 30 is defined by a proximal shoulder 32 projecting inwardly from surface 28 and a segmented distal shoulder 34 projecting inwardly from surface 28 having openings 36 between segments 38. The adapter includes a valve mechanism 40 contained within chamber 30 for selectively obstructing and allowing fluid flow through passageway 26. Valve mechanism 40 includes an elongate resilient member 42 with an axis A' substantially coaxial to Axis A of body 20. Resilient member 42 has a distal end 44 and a proximal end 46. Resilient member 42 is axially compressed between proximal shoulder 32 and distal shoulder 34. The compression of resilient member 42 biases valve 40 to a normally closed position where proximal end 46 forms a fluid tight seal with proximal shoulder 32 and obstructs fluid flow through passage 26. Adapter 10 further includes a pusher 50 for selectively further axially compressing resilient member 42 so that proximal end 46 no longer forms the fluid tight seal with proximal shoulder 32, thereby opening valve 40 and allowing fluid flow through the passageway. Preferably chamber 30 includes plurality of axial channels 31 to facilitate fluid flow around elongate resilient member 42 when valve 40 is open.

Proximal end 22 and distal end 24 of adapter 10 include fittings 60 and 64 respectively to facilitate attachment of fluid delivery and access devices. Preferably fitting 60 at proximal end 24 includes a female luer fitting and fitting 64 at distal end 24 includes a male luer fitting as shown in the drawings. Fittings 60 and 64 may also include other types of fitting for particular applications. The only requirement would be that a delivery device 70 having a fitting 72 to be mounted on fitting 60 at proximal end 22 of the adapter engage pusher 50 in order to open valve 40 when the delivery device is mounted. Preferably the material used to form pusher 50 is less resilient than resilient member 42 when so that when the pusher is engaged by the delivery device, the resilient member will be further axially compressed. The other types of fittings may include, but are not limited to threads, snap-fit, bayonet and the like.

Preferably valve 40 includes a chamfered surface 47 on proximal end 46 of resilient member 42 that engages a conjugate frusto-conical surface 49 located on proximal shoulder 32 that is coaxial to longitudinal axis A of the body.

Preferably, pusher 50 has a proximally extending portion 55 extending proximally within proximal end 22 so that mounting of fluid delivery device 70 will engage pusher 50 thereby further axially compressing resilient member 42, opening valve 40 so that fluid may flow through passageway 26. More preferably, portion 55 extends into proximal female luer fitting 60 so that when the fluid delivery device fitting has a male luer 72 mounted on preferred female luer 60 at the proximal end, male luer 72 will engage pusher 50. The engagement of pusher 50 further axially compresses resilient member 42 and opens valve 40 so that fluid may flow through the passageway.

Figure 4:
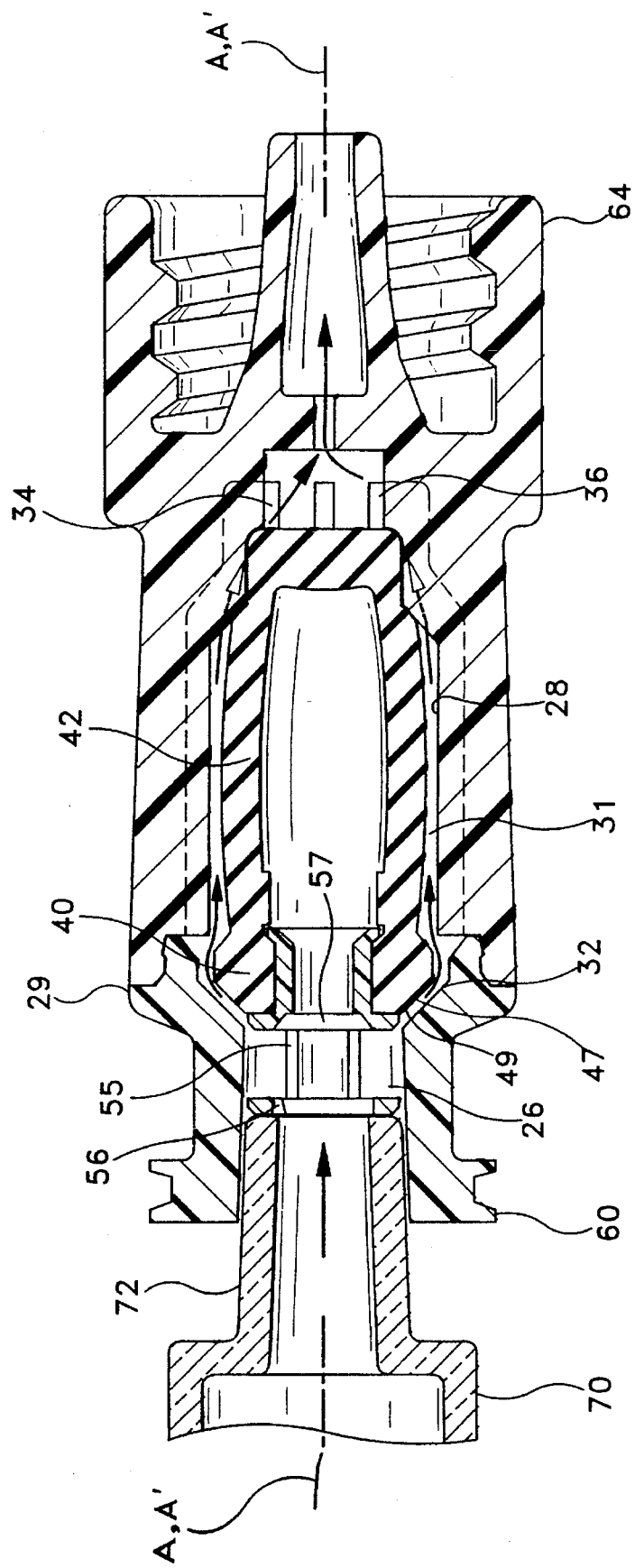
FIG. 4 is a cross-sectional view of the adapter of FIG. 1.

In FIG. 4, the cross-sectional view of the adapter 10 shows fluid delivery device 70 with male luer 72 mounted on female luer 60 and contacting portion 55 of pusher 50 so that the pusher axially further compresses resilient member 42 thus separating chamfer surface 47 from frustoconical surface 49 opening valve 40 and allowing fluid flow from delivery device 70 through the passageway.

Pusher 50 preferably includes at least one passage provision 56 to facilitate fluid flow from delivery device 70 into adapter 10. Passage provisions 56 additionally serve to prevent the male connector tip of device 70 from sealing itself to the surface of pusher 50. In this embodiment, pusher 50 also preferably includes a passageway 58 therethrough that is substantially coaxial to axis A of the body.

Referring to FIGS. 1–4, a method for assembling a valved adapter 10 includes providing body portion 20 having longitudinal axis A, proximal first end 22 and distal second end 24 with passageway 26 therethrough having inside surface 28. The passageway has chamber 30 defined by proximal shoulder 32 and segmented distal shoulder 34 projecting inwardly from surface 28. Distal shoulder 34 has openings 36 therethrough between segments 38. Chamber 30 is intermediate first end 22 and second end 24. Body 20 preferably includes two parts, a proximal body part 23 and a distal body part 25, with a parting line 29 transverse axis A located intermediate proximal shoulder 32 and distal shoulder 34.

The method includes providing valve 40 for containment within chamber 30 for selectively obstructing and allowing fluid flow through passageway 26. The valve includes elongate resilient member 42. The method further includes providing pusher 50 for selectively further compressing elongate resilient member 42 to allow fluid flow.

The method of assembly includes placing elongate resilient member distal end 44 in distal body part 25 so that distal end 44 contacts distal shoulder 34 and the parts are coaxially aligned. Pusher 50 is then axially placed within proximal end 46 of elongate resilient member 42, so that pusher proximal extension 55 extends proximally. Proximal body portion 23 is then placed in coaxial alignment with distal body part 25 and placed over pusher proximal extension 55 and elongate resilient member 42. Proximal body part 23 is then axially advanced to distal body part 25 so that frustoconical surface 49 on proximal shoulder 32 contacts chamfer surface 47 axially compressing resilient elongate member 42 biasing valve 40 in the normally closed position. The assembly is completed by fixedly attaching proximal part 23 to distal part 25. Methods of bonding molded parts known in the art such as adhesive, solvent, spin welding, press-fitting, thermal welding, RF welding, ultra-sonic welding and the like may be used.

In a preferred embodiment where body 20 is formed from polycarbonate, solvent bonding is preferred, but other methods known in the art of plastic bonding are satisfactory. Depending on the material and the bond method selected, the step of placing the resilient member 42 may occur after bonding part 23 to part 25, followed by placing pusher 50.

Figure 6:
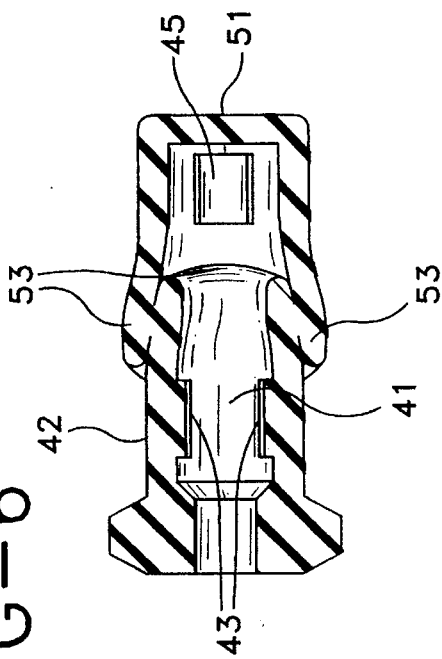
FIG. 6 is a cross sectional view of the elongate resilient member as shown in FIG. 5 along the line 6, 6.
Figure 7:
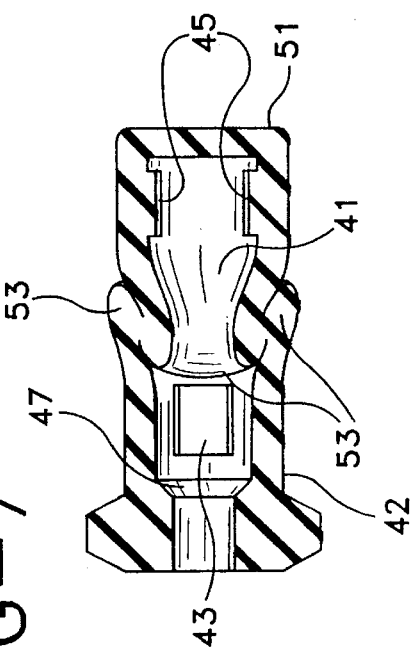
FIG. 7 is a cross sectional view of the elongate resilient member as shown in FIG. 5 along the line 7, 7.
Figure 5:
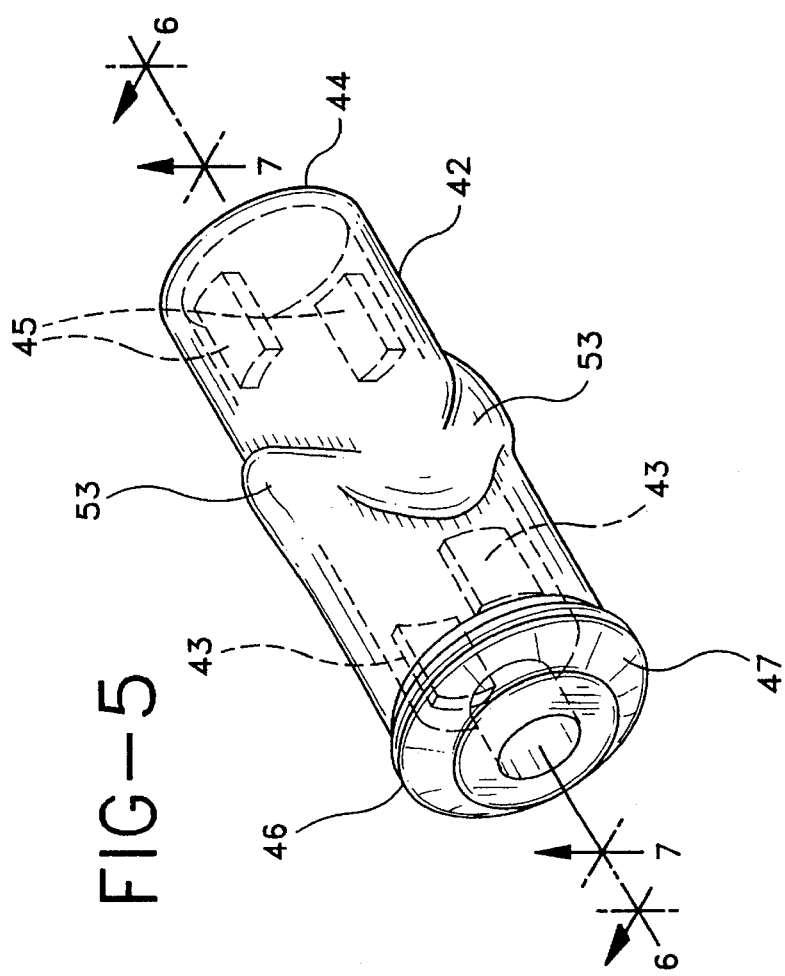
FIG. 5 is a perspective view of the elongate resilient member shown folded or collapsed as it would be under further axial compression, i.e. , the valve in the open position.

Since, according to industry standards, a fluid delivery device male luer fitting may vary in engagement length within a female luer as much as 2.5mm and still be considered within the standard, it is important that a valved adapter, in the embodiment where the fitting at proximal end 22 is a female luer fitting, be able to accommodate all acceptable variants and still function. FIGS. 5, 6 and 7 display elongate resilient member 42 in the further axially compressed state, i.e., where proximal end 46 no longer forms the fluid tight seal with the proximal shoulder. Resilient member 42 has an internal cavity 41 having internal projections 43 to retain pusher 50 within the proximal portion of the resilient member. Cavity 41 includes internal ribs 45 which, along with projection 43, serve to direct the collapse of the resilient member under further axial compression to a region of collapse 53 which allows pusher 50 a greater range of travel than would be possible if only axial compression were utilized. Resilient member 42 of the present invention with the directed collapse provided by cavity 41, projections 43 and ribs 45 allows male luer fitting 72 at the "long" (i.e., "thin") end of the allowable dimension to be fully mounted and also allows for a male luer 72 at the "short" (i.e., "fat") end of the dimension to open the valve. FIGS. 6 and 7 demonstrate how the resilient member collapses showing the directed region of collapse 53.

Resilient member 42 also includes an area 51 located at distal end 44 substantially transverse axis A' suitable to serve as a septum. Area 51 allows devices such as guidewires, stylets, needles and probes to be passed through the adapter into the vascular access device. Area 51 may have a frustoconical or other shape to provide a lead in surface for devices to be passed through to the septum area and also may be preslit to facilitate passage of the devices.

Adapter 10 may also include provisions for closing the proximal female luer fitting 60 and the distal male luer 64. These provisions may include, but are not limited to, a tethered plug 80 having a plug portion 81 sized to occlude passageway 26 at proximal luer fitting 60. Plug 80 may include an outwardly extending lip 82 to facilitate handling and a tether 83 sized to fit over proximal luer fitting 60 and retain the plug. Alternatively luer fitting 60 may be covered with a cap 84 sized to fit luer fitting 60. A cap 90 sized to fit distal male luer fitting 64 may be used to close male luer fitting 64.

Components for the body portion of the valved adapter may be formed from plastic resins such as polystyrene, polycarbonate, polypropylene, polysulfone, polyacetal, polyamide, polyacrylate, polyvinylchloride, alloys of polystyrene, polycarbonate, polypropylene, polyacetal, polyamide, polysulfone, polyacrylate and polyvinylchloride as well as others which have the required properties of dimensional stability and strength. The preferred resin is polycarbonate which is preferably injection molded to form proximal and distal body portions, preferably including proximal female luer fitting 60 and distal male luer fitting 64. Elongate resilient member 42 may be formed from natural rubber, chloroprene, thermoplastic elastomers, silicone rubber, ethylene-propylene-diene monomer (EPDM) or other elastomers having low compression set tendencies and suitable biocompatability. Preferably, the elongate member is formed by compression molding from silicone rubber having a durometer between about 45 and about 70 Shore A.

The tethered plug 80 used to close female luer fitting 60 may be formed from natural rubber, chloroprene, silicone rubber, EPDM and the like. Preferably, tethered plug 80 is formed by compression molding from silicone rubber. Cap 84 for female luer fitting 60 and cap 90 for male luer fitting 64 may be formed from polystyrene, polycarbonate, polyethylene, polyvinyl chloride, polypropylene, polyacetal and the like, preferably these caps are formed by injection molding from polyethylene.

The valved adapter of the present invention has a low internal volume, is easily attached to medical access devices such as catheters, feeding tubes or other infusion devices to allow rapid mounting and dismounting of fluid handling devices with minimal fluid loss or air entrainment during mounting and dismounting. Additionally, the valved adapter of the present invention allows introduction of stylets, probes, guidewires and the like into the medical access device while retaining the ability to rapidly mount and dismount fluid handling devices with rapid automatic startup and shutoff and includes with the tethered plug or cap provisions for closing the proximal end when there is no delivery device mounted.

What is claimed is:

1. A method for assembling a valved adapter for a medical access device comprising:

providing a substantially cylindrical body with a longitudinal axis having a proximal first end with a female luer fitting, a distal second end with a male luer fitting and a passageway having an inside surface therethrough, said passageway having a chamber defined by a proximal shoulder projecting inwardly from said surface of said passageway and a segmented distal shoulder projecting inwardly from said surface of said passageway, said distal shoulder having openings therethrough between said segments, said chamber being intermediate said first end and said second end, said body comprising a distal part and a proximal part having parting line transverse said longitudinal axis located intermediate said annular shoulders;

providing a valve for containment within said chamber for selectively obstructing and allowing fluid flow through said passageway, said valve comprising an elongate resilient member having an axis substantially coaxial to said longitudinal axis of said body and having a distal end and a proximal end, said resilient member being axially compressed between said proximal shoulder and said distal shoulder, said compression of said resilient member biasing said valve to a normally closed position wherein said proximal end of said resilient member forms a fluid tight seal with said proximal shoulder thereby obstructing fluid flow through said passageway;

providing a pusher for selectively further compressing said elongate resilient member so that said proximal end of said resilient member no longer forms said fluid tight seal with said proximal shoulder thereby allowing fluid flow through said passageway, said pusher including a proximal extension;

placing said elongate resilient member in said distal part so that said distal end of said elongate resilient member is in contact with said segmented distal shoulder and said resilient member axis is substantially coaxial with said body axis;

placing said pusher in said elongate resilient member so that said proximal extension of said pusher extends proximally from said resilient member;

placing said proximal part of said body on said distal part of said body so that said proximal end of said elongate resilient member contacts said proximal shoulder, with said proximal extension of said pusher means extending into said proximal part thereby containing said elongate resilient member within said chamber and compressing said elongate resilient member; and fixedly attaching said proximal part on said distal part of said body thereby forming said valved adapter.

2. The method of claim 1 with said fixedly attaching step being a method selected from the group consisting of solvent bonding, adhesive bonding, spin welding, press fitting, thermal welding, RF welding and ultrasonic welding.

3. The method of claim 1 wherein said step for providing said cylindrical body includes providing a body having distal attachment means for attaching said adapter to a medical access device and proximal attachment means for mounting a fluid delivery device.

4. The method of claim 1 further including providing a plug sized to fit within said proximal female luer fitting for closing said female luer fitting, said plug having a tether for placement onto said cylindrical body.

5. A valved adapter for a medical access device comprising:

a body with a longitudinal axis having a proximal first end including a female luer fitting, a distal second end including a male luer fitting and a passageway therethrough having an inside surface, said passageway having a chamber defined by a proximal shoulder and a segmented distal shoulder projecting inwardly from said surface of said passageway, said distal shoulder having openings therethrough between said segments, said chamber being intermediate said first end and said second end;

a valve contained within said chamber for selectively obstructing and allowing fluid flow through said passageway, said valve comprising an elongate resilient member having an axis substantially coaxial to said longitudinal axis of said body and having a distal end and a proximal end, said resilient member being axially compressed between said proximal annular shoulder and said distal annular shoulder, said compression of said elongate resilient member biasing said valve to a normally closed position wherein said proximal end of said resilient member forms a fluid tight seal with said proximal shoulder thereby obstructing fluid flow through said passageway; and a pusher for selectively further axially compressing said elongate resilient member so that said proximal end of said elongate resilient member no longer forms said fluid tight seal with said proximal shoulder thereby opening said valve and allowing fluid flow through said passageway.

6. The adapter of claim 5 wherein said chamber includes a plurality of channels for facilitating fluid flow around said elongate resilient member when said valve is open.

7. The adapter of claim 5 wherein said fluid tight seal comprises a chamfered surface on said proximal end of said elongate resilient member engaging a conjugate frusto conical surface located on said proximal shoulder coaxial said longitudinal axis of said body.

8. The adapter of claim 5 wherein said pusher has a proximally extending portion within said proximal end of said body so that an attachment of a fluid handling device at said proximal end of said body will engage said pusher thereby further compressing said resilient member so that fluid may flow through said passageway.

9. The adapter of claim 8 wherein said pusher having said proximally extending portion includes a surface within said female luer fitting so that when a fluid handling device having a male luer fitting is mounted on said proximal end having said female luer fitting, said male luer fitting will engage said pusher thereby further compressing said resilient member so that fluid may flow through said passageway.

10. The adapter of claim 9 wherein said surface of said proximally extending portion of said pusher further includes at least one passage provision to facilitate fluid flow from the male luer fitting into said adapter from the male luer fitting.

11. The adapter of claim 9 wherein said distal end of said elongate resilient member includes an area substantially transverse said longitudinal axis suitable to serve as a septum and said pusher has a passageway therethrough substantially coaxial with said longitudinal axis and transverse said septum area so that a device selected from the group consisting of guidewires, stylets, needles and probes may be passed through said septum and said adapter into the medical access device.

12. The adapter of claim 11 wherein said septum area further includes a slit for facilitating the passage of said devices selected from said group through said adapter.

13. The adapter of claim 5 wherein said proximal end further includes a substantially cylindrical resilient plug having a diameter sized to have an interference fit within and close said female luer fitting and a tether including a loop fixedly attached to said plug and sized to be retained on said cylindrical body.

14. The adapter of claim 5 wherein said proximal end further comprises a cap for a female luer fitting.

15. The adapter of claim 5 wherein said cylindrical body portion is formed from a resin selected from the group consisting of polystyrene, polycarbonate, polypropylene, polyacrylate polytetrafluoroethylene, polyethylene, polyacetal, polyamide, polysulfone, polyvinylchloride and alloys thereof.

16. The adapter of claim 5 wherein said elongate resilient member is formed from a material selected from the group consisting of natural rubber, chloroprene, thermoplastic elastomer, silicone rubber and ethylene-propylene-diene-monomer.

17. The adapter of claim 5 wherein said pusher is formed from a resin selected from the group consisting of polyethylene, polysulfone, polycarbonate, polyacrylate, polypropylene, polyvinylchloride and polystyrene.

18. A valved adapter for a medical access device comprising:
 a substantially cylindrical body with a longitudinal axis having a proximal first end, said proximal end of said body comprises a female luer fitting, a distal second end having a male luer fitting and a passageway having an inside surface therethrough, said passageway having a chamber defined by a proximal shoulder projecting inwardly from said surface of said passageway and a segmented distal shoulder projecting inwardly from said surface of said passageway, said distal shoulder having openings therethrough between said segments;
 a valve contained within said chamber for selectively obstructing and allowing fluid flow through said passageway, said valve comprising an elongate resilient member having an axis substantially coaxial to said longitudinal axis of said body and having a distal end and a proximal end, said resilient member being axially compressed between said proximal shoulder and said distal shoulder, said compression of said resilient member biasing said valve to a normally closed position wherein said proximal end of said resilient member forms a fluid tight seal with said proximal shoulder thereby obstructing fluid flow through said passageway; and
 a pusher for selectively further axially compressing said elongate resilient member, said pusher having a proximally extending portion within said female luer fitting so that when a fluid handling device having a male luer fitting is mounted on said proximal end having said female luer fitting, the male luer fitting will engage said pusher thereby further axially compressing said elongate resilient member so that said proximal end of said elongate resilient member no longer forms said fluid tight seal with said proximal shoulder thereby opening said valve and allowing fluid flow through said passageway.

19. The valved adapter of claim 18 wherein said chamber further includes a plurality of channels for facilitating fluid flow around said elongate resilient member when said valve is open.

* * * * *